United States Patent [19]

Sotman et al.

[11] 4,017,974

[45] Apr. 19, 1977

[54] HANDPIECE WITH ADJUSTABLE WATER SPRAY

[75] Inventors: Kurt Sotman, Penn Wynne; John E. Nash, Downingtown, both of Pa.

[73] Assignee: Star Dental Manufacturing Co., Inc., West Conshohocken, Pa.

[22] Filed: Sept. 30, 1974

[21] Appl. No.: 510,280

[52] U.S. Cl. .................................................. 32/28
[51] Int. Cl.² ........................................... A61C 1/68
[58] Field of Search ...................................... 32/28

[56] References Cited

UNITED STATES PATENTS 2,437,017  3/1948  Cunningham ..................... 32/28

FOREIGN PATENTS OR APPLICATIONS 1,107,890  5/1961  Germany ......................... 32/28

*Primary Examiner*—Robert Peshock
*Attorney, Agent, or Firm*—Caesar, Rivise, Bernstein & Cohen

[57] ABSTRACT

Improved means for directing an atomized water spray at the tip of a bur in a dental handpiece irrespective of the length of the bur. The means comprises a water carrying tube terminating at a free end adjacent to the bur and directed at the bur at a first predetermined acute angle with respect to the longitudinal axis of the bur, a first air carrying tube disposed on one side of the water tube and having a free end terminating adjacent the free end of the water tube and a second predetermined acute angle to the longitudinal axis of the bur, the second angle being greater than the first angle, and a second air carrying tube disposed on the outer side of the water tube and having a free end terminating adjacent the free end of the water tube and at a third predetermined acute angle with respect to the longitudinal axis of the bur, the third angle being smaller than the first angle. Metering means are provided for varying the flow through the air tubes to effect the control of the direction of the atomized spray.

In accordance one aspect of the invention, the free ends of the air tubes also extend in a first plane directed laterally to one side of the bur while the water tube is directed laterally to the other side of the bur to thereby compensate for any lateral deflection of the atomized spray resulting from windage caused by the rotating bur.

11 Claims, 8 Drawing Figures

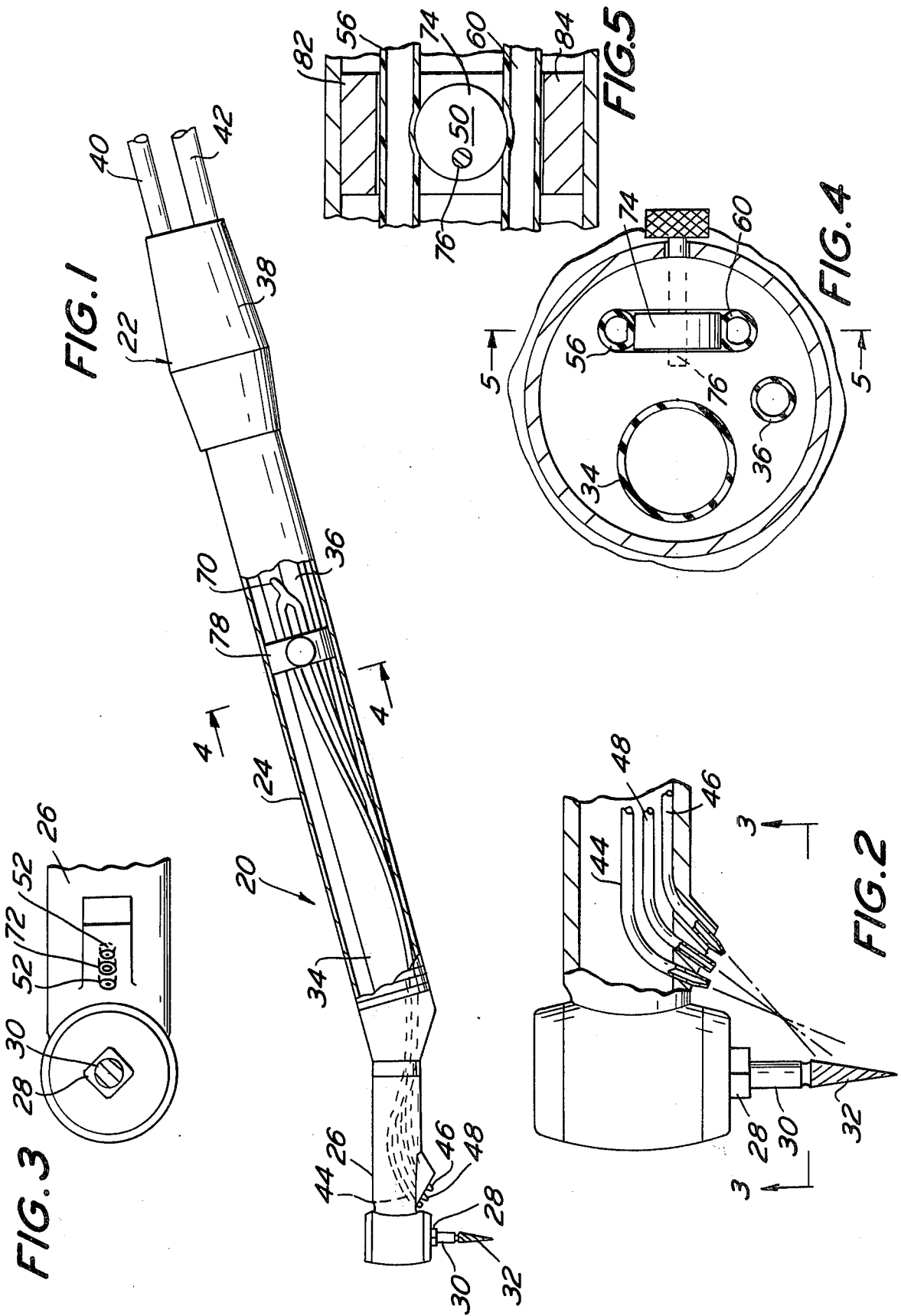

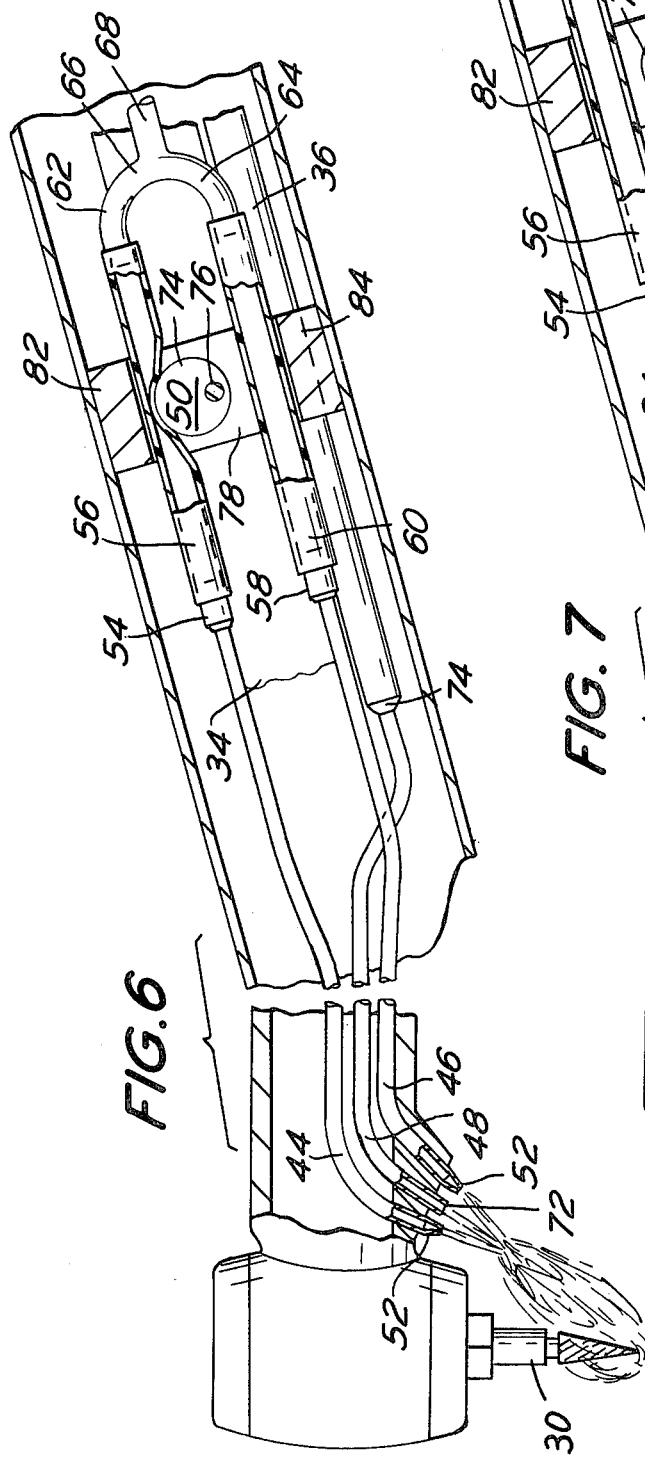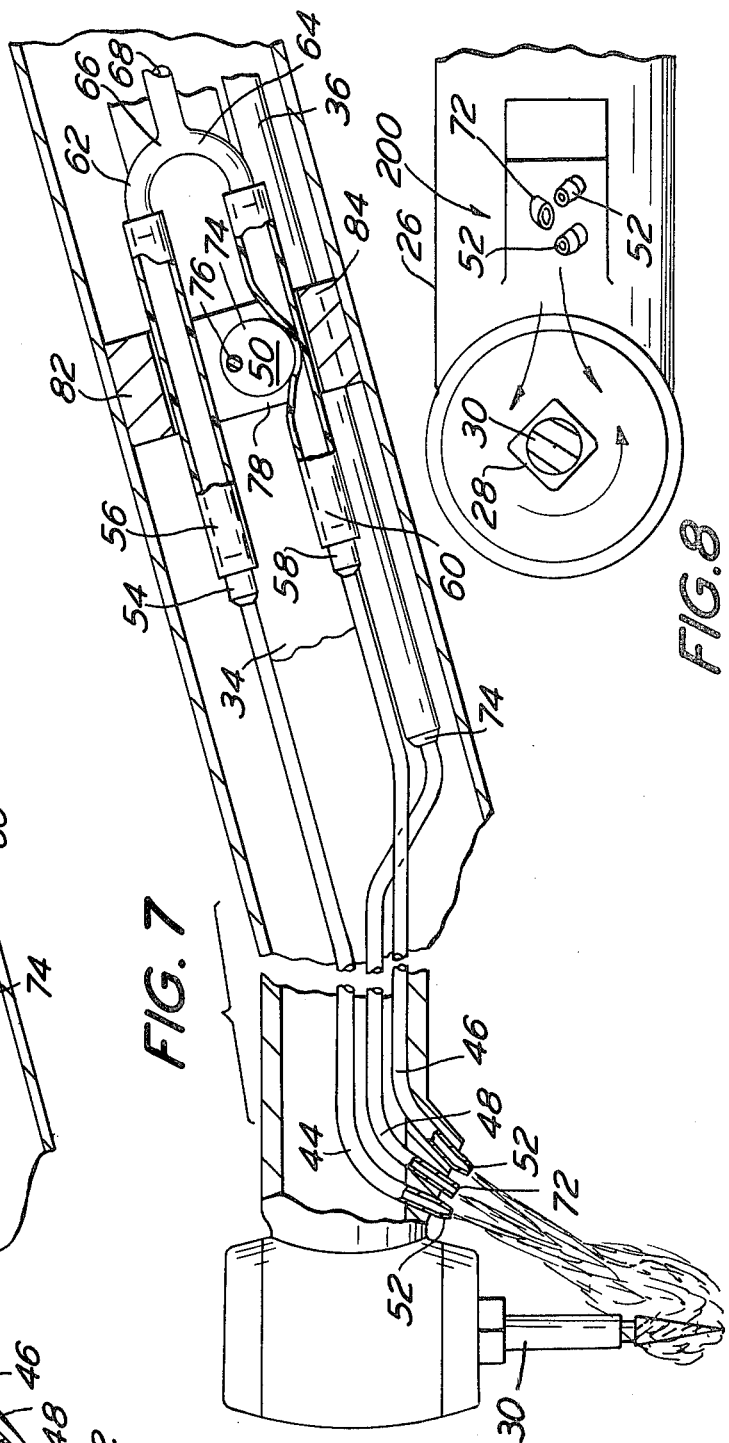

HANDPIECE WITH ADJUSTABLE WATER SPRAY

This invention relates generally to dental handpieces, and more particularly to dental handpieces having means for directing an atomized water spray at the cutting bur.

Modern dental drilling equipment commonly operate the dental cutting tool at speeds of upwards of 200,000 r.p.m. Such high cutting speeds necessarily result in the generation of large amounts of frictional heat in the tooth being drilled. In order to cool this tooth it is almost a universal practice to direct a water spray against the tooth during the drilling operation.

Various techniques have been proposed and are presently utilized to direct the spray at the tip of the cutting tool or bur. Such techniques commonly involve the physical movement of the spray directing tubes to adjust the spray to impact the tip of the bur.

For example, in U.S. Pat. No. 3,199,196 and U.S. patent application Ser. No. 217,745, filed on Jan. 14, 1972, both assigned to the same assignee of this invention, there is shown in dental handpieces several types of spray means for creating an atomized spray and for directing the spray at the tip of the cutting bur. Such means comprise a collar mounted on and adapted to slide along the body of the handpiece, an air tube and water tube. The tubes are coupled to the collar and include openings in their respective free ends for mixing the fluids carried thereby to form an atomized spray. By sliding the collar along the tube, the tubes are moved thereby such that the spray can be directed at the tip of the bur irrespective of the length thereof.

While prior art adjustable spray heads or clips have proved capable of accomplishing their intended prupose, in the interest of simplicity and ease of cleaning the handpiece it is desirable to provide a readily adjustable directable spray without moving the water and air tubes.

Accordingly, it is a general object of this invention to overcome the disadvantages of the prior art adjustable spray devices for dental handpieces.

It is a further object of this invention to provide, in a dental handpiece, a spray device capable of the ready adjustment of the direction of the spray.

It is still a further object of this invention to provide in a dental handpiece a stationary spray device capable of adjusting the direction of the spray without moving any fluid carrying tubes.

It is yet a further objection of this invention to provide in a dental handpiece stationary spray device which compensate for spray deflection resulting from windage produced by the rotation of the cutting bur.

These and other objects of this invention are achieved by providing in a dental handpiece adapted for use with various lengths of cutting burs improved means for providing an atomized water spray and for adjusting the direction of the spray to the tip of the bur irrespective of the length of the bur. The spraying means comprises a tube for carrying water having a free and generally directed at the bur and a first tube for carrying compressed air, located laterally of the water tube and having a free end disposed adjacent the free end of the water tube. The compressed air and the water mix at the free ends of the tubes to create an atomized water spray. The spray means also include metering means for varying the flow air through the air tube to effect the control of the direction of the atomized spray.

In accordance with another aspect of the invention the free end of the water tube is also directed to one side of the bur and the free end of the air tube is directed at the other side of the bur to compensate for any lateral deflection of the atomized spray resulting from the windage caused by the rotating bur.

Other objects and many of the attendant advantages of this invention will readily be appreciated as the same becomes better understood by reference to the following detailed description when considered in connecton with the accompanying drawing wherein:

FIG. 1 is a side elevational view, partially broken away, of a complete dental handpiece embodying the present invention;

FIG. 2 is an enlarged side elevational view of the portion of the handpiece shown in FIG. 1 partly broken away to show details of the spray device of this invention;

FIG. 3 is a sectional view taken along line 3—3 of FIG. 2;

FIG. 4 is an enlarged sectional view taken along line 4—4 of FIG. 1;

FIG. 5 is a sectional view taken along line 5—5 of FIG. 4;

FIG. 6 is an enlarged side elevational view of a portion of the handpiece shown in FIG. 1 partly broken away to show the interior of the handpiece during one particular mode of operation of the spray device of this invention;

FIG. 7 is a view, similar to that of FIG. 6 during another mode of opration of the invention;

FIG. 8 is a view, similar to that shown in FIG. 3, but showing an alternative embodiment of this invention.

Referring now in greater detail to the various figures of the drawing wherein like reference characters refer to like parts, a spray device embodying the present invention is shown generally at 20 in FIG. 1

Device 20 is mounted within a conventional dental handpiece shown generally at 22. Handpiece 22 includes a hollow tubular body member 24 having one end 26 projecting angularly from the remainder of the body member in substantially a horizontal plane. Mounted within the end 26 is a rotary chuck 28 (the outwardly projecting end showing in FIGS. 1, 2, 6, 7, and 8). A conventional dental bur 30 is mounted within the chuck. The bur 30 is an elongated member a cutting tip 32 at the free end thereof.

A conduit 34 extends along the entire length of body member 24 and supplies air for rotating an air turbine (not shown) on rotary chuck 28. Conduit 34 additionally supplies the air for the spray means 20 as will be explained hereinafter. A second conduit 36 is also proivded in body member 24. This conduit is used for supplying water to the spray means 20. An end cap 38 is secured on the end of body member 24. Flexible tubes 40 and 42 are connected to conduits 34 and 36, respectively.

The improved spray deflecting means of this invention is best seen in FIGS. 1 and 6.

As can be seen therein, the spraying means 20 basically comprises a pair of air tubes 44 and 46, a water tube 48 and a metering means 50.

The air tubes are elongated tubular members, preferably formed of stainless steel in the interest of durability and appearance. Each tube includes a free end 52 bent at an angle with respect to the remaining portions thereof and forming an air outlet nozzle. The free ends of the tubes extend out of the handle portion 26 and adjacent to the bur 30. The tubes are mounted within end portion 26 so that the exposed free ends extend at different acute angles to the longitudinal axis of the bur but lie in a common plane (see FIG. 3) for reasons to be described later.

The rear end of air tube 44 is connected, via a coupling 54, to one end of a hollow flexible conduit 56. Similarly, the rear end of air tube 46 is connected, via coupling 58, to one end of a hollow flexible conduit 60. The flexible conduits 56 and 60 can be made from flexible plastics and rubber. An example of a flexible tube of plastic tubing that can be used is that sold under the Trademark TYGON. The other ends of flexible tubes 56 and 60 are connected to legs 62 and 64, respectively, of a hollow yoke member 66. The yoke 66 includes an input line 68, which, as can be seen in FIG. 1, is connected to and communicates with the interior of air conduit 34, via a port 70.

The water tube 48, like air tubes 44 and 46, is and elongated tubular member and is also preferably formed of stainless steel. The free end of water tube 48, denoted by the reference numeral 72, is bent at an angle to the remaining portion thereof and forms a water outlet nozzle. The water tube is mounted between the air tubes 44 and 46 in the handle portion 26. The free end 72 of the water tube 48 extends out of the handle portion 26 and between the free ends 52 of the air tubes, with the free end 72 at an acute angle to the longitudinal axis of the bur and lying in the plane of the free ends of the air tubes (See FIG. 3).

For reasons to be described later, the angle with which the free end 72 of the water tube makes with the longitudinal axis of the bur 30 is less than the angle which the free end 52 of tube 46 makes therewith but greater than the angle which free end 52 of air tube 44 makes therewith. In accordance with the preferred embodiment of this invention the free end 72 of the water tube bisects the angle between the free ends 52 of the air tubes 44 and 46. The other end of the water tube 48 is connected, via port 74 (FIG. 6), to water conduit 36.

In order to regulate or meter the flow of air from the air tubes, metering means 20 is provided. It should be noted at this juncture that while the metering means 50 is shown with handpiece 22 it may alternatively be located remotely of the handpiece, that is, upstream therefrom, e.g., at a console.

The operation of the metering means will be described in detail later. Suffice to say at this time that the metering means is operative for adjusting the air flow through the air tubes 44 and 46 such that the flow through one may exceed the other, be equal to the other, or be less than the other. This feature, in conjunction with the angle at which the free ends of the air tubes 44 and 46 and the water tube 48 extend enables one to readily adjust the angle at which the spray leaves the free ends of those tubes. Accordingly, the spray can be adjusted as desired toward or away from chuck 28 to thereby impact the tip 32 of the bur 30 irrespective of the length of the bur.

For example, since the free end of tube 44 makes a greater angle with respect to the longitudinal axis of the bur 30 than does the free end of the tube 46, with the free end of the water tube extending therebetween, should the flow of air through tube 44 exceed that through tube 46, the angular momentum imparted to the spray by the air from tube 44 exceeds that imparted to the spray from tube 46 and the spray is directed downward and away from the chuck 38. With the spray means 20 of this invention in such a mode of operation the spray can be directed at relatively long burs as shown in FIG. 7.

If it is desired to utilize a shorter bur the spray should be directed closer to the chudk 38. To that end, the flow of air through tube 44 is made less than that through tube 46, whereupon the angular momentum imparted to the spray by the air exiting tube 46 exceeds that of tube 44. This action results in the deflection of the spray upward and toward chuck 38. Such a mode of operation is shown in FIG. 6.

As will be appreciated by those skilled in the art when the air flow through air lines 44 and 46 is equal, the spray wil be directed to a point a distance from the chuck intermediate that shown in FIGS. 6 and 7.

In accordance with the preferred embodiment of this invention, the metering means 50 comprises an eccentric cam 74 fixedly mounted on a rotatable shaft 76. The shaft is disposed intermediate to flexible conduits 56 and 60 and is mounted for rotation in a bracket 78 (FIG. 1). One end of the shaft extends through an opening (not shown) in the body 24. A knurled knob 80 (FIG. 4) is connected to the end of the shaft which extends out of the body 24. The knob 80 is provided to enable the user of the handpiece to rotate the cam by rotating the knurled knob.

A pair of pads 82 and 84 (FIGS. 6 and 7) are disposed within the body 24 between flexible tubes 56 and 60, respectively, and in line with cam 74.

The cam is so dimensioned that when rotated about shaft 76 to the position shown in FIG. 6 it substantially stops the flow of air through air tube 44 and when in the position shown in FIG. 7 it substantially stops the flow of air through tube 46. When in the intermediate position, like that shown in FIG. 5, the cam reduces the flow of air through both tubes equally.

The cam is frictionally loaded by means (not shown) to maintain it in a pre-set position, like that shown in FIG. 5.

Accordingly, it should be appreciataed that by the rotation of the knurled knob on the handle, the user of the handpiece can alternately "pinch" either air tube to proportion the flows through the respective air tubes.

The water content of the spray is adjusted by varying the water flow rate through conduit 36 by means (not shown).

The combined flow restriction, that is, the total cross section through air tubes 44 and 46 remains fairly constant for all positions of the cam 74, such that the total air flow is relatively unaffected by changes in the spray direction. Therefore, no re-setting of the water content of the spray is required when changing its direction since the air-water ratio is maintained.

As noted heretofore all of the free ends of the tubes 44, 46 and 48 lie in a common plane. As can be seen in FIG. 3, the bur 30 also lies in this plane such that the spray is not only directed the required distance from the chuck 28, but also such that it is directed in the plane of the bur to therby reach the tip area. In some cases it may be desirable to offset the plane of the tubes 44, 46 and 48 laterally to the side of the plane of the bur to compensate for any deflection of the spray which would result from windage produced by the rotation of the bur.

In FIG. 8, there is show an alternative embodiment of the spraying means 20 which accomplishes the ends sought by such means while also compensating for windage deflection without necessitating offsetting of the air and water tubes laterally of the plane of the bur. Such alternative spraying means is denoted by the reference numeral 200. Preferably the spraying means 200 is contructed in a similar manner in all respects to that of spraying means 20, except that the free ends of the air tubes 44 and 46 and the water tube 48 do not lie in the same plane as that of bur 30, as is the case with the tubes of spraying means 20.

As can be seen in FIG. 8, the free ends 52 of the air tubes 44 and 46 lie in a common plane which is at slight angle to the plane in which th bur 30 lies. Accordingly, the direction of flow of a fluid exiting from the air tubes follows that plane to a position slightly to the side of the bur and adjacent its tip. The free end 72 of the water tube 48 lies in a plane which is also at an acute angle to the plane that the bur lies in but is directed to the opposite side thereof such that the direction of the fluid exiting from the water tube follows the plane of that tube to a position slightly on the other side of the bur and adjacent its tip.

By regulating or proportioning the flow of water and air flowing through the respective tubes, the spray which is produced thereby can be directed to either side of the bur as is desired (as is denoted by the arrows shown in FIG. 8). This is of considerable importance in that it enables the spray to be directed to various lateral positions with resepct to the bur to compensate for any deflection of the spray which would occur as a result of the windage produced by the rotating bur. Accordingly, the spray can be directed precisely to the point at which the tip of the bur makes contact with the tooth being drilled.

Although the spray device of this invention has been described specifically for use with an air driven dental drill, it is to be understood that it can be used equally well with a water driven, belt driven or electrically driven drill.

Without further elaboration, the foregoing will so fully illustrate my invention that may, by applying current or future knowledge, readily adapt the same for use under various conditions of service.

What is claimed as the invention is:

1. For use with a dental handpiece adapted for use with various length cutting burs the improvement comprising means for providing an atomized water spray and for adjusting the direction of the spray to the tip of the bur irrespective of the length of said bur, said means comprising a tube for carrying water and having a free end generally directed at said bur, a first tube for carrying compressed air located laterally of said water tube and having a free end disposed adacent the free end of the water tube, a second tube for carrying compressed air located laterally of said water tube and having a free end disposed adjacent the free end of said water tube, the compressed air and water mixing at the free end of the water tube to create an atomized water spray, and metering means for varying the flow of air through said first air tube and said second air tube to effect the control of the direction of the atomized spray.

2. The handpiece of claim 1 wherein said first and second air tubes are located on opposite sides of said water tube.

3. The handpiece of claim 2 wherein said free end of said water tube is directed at a first predetermined acute ange to the longitudinal axis of said bur.

4. The handpiece of claim 3 wherein the free end of the first water tube is directed at a second acute angle to the longitudinal axis and wherein the free end of the second water tube is directed at a third acute angle to the longitudinal axis of the bur, said second angle bearing smaller than said first angle and said third angle being larger than said first angle.

5. The handpiece of claim 4 wherein the free ends of all of said tubes lie in a common plane.

6. The handpiece of claim 4 wherein the free end of said first and second air tubes also extend in a first common plane directed to one side of said bur and wherein the free end of the water tube also is directed to the other side of said bur, the direction at which said free ends extend serving to compensate for any lateral deflection of the atomized spray resulting from the windage caused by the rotating bur.

7. The handpiece of claim 4 wherein said metering means adjusts the flow of air through said air tubes by effecting the pinching of said tubes.

8. The handpiece of claim 7 wherein said metering means comprises at least one cam for effecting the pinching of said air tubes.

9. The handpiece of claim 8 wherein said metering means comprises a single cam located between said air lines and remote from the free ends thereof, whereupon the rotation of said cam effects an increase in air flow through one air tube and a concomitant decrease in air flow through the other air tube.

10. The handpiece of claim 10 wherein said cam is arranged to equalize the air flow through both of said air tubes.

11. In a dental handpiece having a rotating cutting bur and an atomized water spray directed generally at said bur, the improvement comprising means to accurately direct the spray at said bur and compensate for any spray deflection resulting from the windage created by the rotating bur, said means comprising a tube for carrying water having a free end located adjacent the bur and directed at an angle slightly to the side of said bur, a first tube for carrying compressed air and having a free end disposed adjacent the free end of the water tube and directed at an angle slightly to the opposite side of said bur, a second tube for carrying compressed air having a free end located adjacent the bur and directed at an angle slightly to the side of said bur, the free end of both of said air tubes being directed at the same lateral angle with respect to said bur, and means to meter the air flowing through said air tubes.

* * * * *